(12) United States Patent
Boiko

(10) Patent No.: US 8,527,071 B2
(45) Date of Patent: Sep. 3, 2013

(54) ADAPTIVE CONTROL SYSTEM FOR A SULFUR RECOVERY PROCESS

(75) Inventor: Igor Boiko, Calgary (CA)

(73) Assignee: IMB Controls Inc., Calgary (CA)

( * ) Notice: Subject to any disclaimer, the term of this patent is extended or adjusted under 35 U.S.C. 154(b) by 60 days.

(21) Appl. No.: 13/049,697

(22) Filed: Mar. 16, 2011

(65) Prior Publication Data
US 2012/0237438 A1    Sep. 20, 2012

(51) Int. Cl.
*G05B 13/02* (2006.01)
*C01B 17/02* (2006.01)

(52) U.S. Cl.
USPC .......... 700/28; 700/42; 423/573.1; 423/574.1

(58) Field of Classification Search
None
See application file for complete search history.

(56) References Cited

U.S. PATENT DOCUMENTS

| 4,100,266 | A | * | 7/1978 | Smith | 423/574.1 |
|---|---|---|---|---|---|
| 4,376,026 | A | * | 3/1983 | Hoffman et al. | 204/407 |
| 5,266,274 | A | * | 11/1993 | Taggart et al. | 422/112 |
| 5,754,436 | A | * | 5/1998 | Walsh et al. | 713/300 |
| 2004/0030414 | A1 | * | 2/2004 | Koza et al. | 700/1 |
| 2006/0121616 | A1 | * | 6/2006 | Lefebvre et al. | 436/55 |
| 2006/0133971 | A1 | * | 6/2006 | Sun et al. | 422/198 |

* cited by examiner

*Primary Examiner* — Melvin C Mayes
*Assistant Examiner* — Sheng H Davis

(57) ABSTRACT

Control of a process for producing free sulfur from hydrogen sulfide is accomplished by manipulating the flow rate of a feed stream containing oxygen to a furnace in such a manner that a desired proportion of the hydrogen sulfide fed to the furnace is converted to sulfur dioxide. Combustion of hydrogen sulfide is precisely controlled by the proposed system to maintain the hydrogen sulfide and sulfur dioxide concentrations in the tail gas at acceptable levels to minimize the environmental pollution.

7 Claims, 4 Drawing Sheets a.

b.

US 8,527,071 B2

ADAPTIVE CONTROL SYSTEM FOR A SULFUR RECOVERY PROCESS

CROSS-REFERENCE TO RELATED APPLICATIONS

U.S. Patent Documents:

| | | | |
|---|---|---|---|
| 3,026,184 | March 1962 | Karaser | 422/62. |
| 3,312,529 | April 1967 | Evano | 422/62. |
| 3,871,831 | March 1975 | Andral et al. | 422/62. |
| 4,021,201 | May 1977 | Vautrain et al. | 422/110. |
| 4,100,266 | July, 1978 | Smith | 423/574. |
| 4,543,245 | September 1985 | Peterman et al. | 423/574. |
| 5,176,896 | January 1993 | Bela | 423/574. |
| 5,266,274 | November 1993 | Taggart et al. | 422/112. |
| 5,965,100 | October 1999 | Khanmamedov | 423/576. |
| 7,501,111 | March 2009 | Keller et al. | 423/573. |
| 7,754,471 | July 2010 | Chen | 435/266. |

Foreign Patent Documents:

| | | | |
|---|---|---|---|
| 1,323,173 | October 1993 | Lagas | CA |

OTHER REFERENCES

J. B. Pfeiffer, *Sulfur Removal and Recovery from Industrial Processes*, Washington, D.C., U.S.A., American Chemical Society, 1975.

I. Boiko, "Dynamical model of the Claus process and its identification," *Proc. 2007 American Control Conference*, New York, USA, pp. 2260-2264.

I. Boiko, *Discontinuous Control Systems: Frequency-Domain Analysis and Design*, Boston, Birkhauser, 2009.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

1. Field of the Invention

This invention relates to an apparatus and method for controlling the combustion of acid gas containing hydrogen sulfide in sulfur recovery units (Claus plants).

2. Prior Art

Sulfur is present in natural gas principally as hydrogen sulfide $H_2S$ and in other fossil fuels as sulfur-containing compounds which are converted to $H_2S$ during processing. The $H_2S$ is removed from the natural gas or refinery gas by means of one of the gas treating processes. The resulting $H_2S$-containing acid gas is processed to recover sulfur. The recovery of free sulfur from gaseous streams containing hydrogen sulfide has become a valuable procedure in the petroleum gas industries. The Claus process is widely used for sulfur recovery from $H_2S$. Conventional Claus plant consists of a thermal conversion section, and a few stages of catalytic conversion section, in series. Acid gas feed entering sulfur recovery unit consists of $H_2S$ and other uncombustible gases (nitrogen, $CO_2$) and sometimes, in small amounts, combustible gases. The combustion in the thermal section is controlled by adding a controlled amount of air, required for burning one-third of the $H_2S$ to react with oxygen to produce $SO_2$. The balance of the conversion is achieved in the presence of catalyst in the catalytic conversion stages provided via the reaction of two-thirds of $H_2S$ and $SO_2$, to produce sulfur and water. Liquid sulfur is then collected in sulfur concentrators. However, not all the amounts of $H_2S$ and $SO_2$ react. Some residual amounts remain in a tail gas. Very strict requirements to the residual $H_2S$ and $SO_2$ make the control of the Claus reaction a difficult problem. Unlike the conventional combustion process, which allows for the use of different fuel-air ratios, the Claus reaction requires the stoichiometric values of $H_2S$ and air. Most commonly, the residual $H_2S$ is further burned and converted into environmentally less harmful $SO_2$ and the latter is emitted. For that reason, excess of either $H_2S$ or $SO_2$ compared to the stoichiometric values increases emissions, and only optimal $H_2S$ to $SO_2$ ratio (corresponding to stoichiometric combustion), which is achieved by proper air-to-acid gas ratio, provides minimal $SO_2$ emissions. Conventional control of the Claus reaction includes an air-to-acid gas ratio controller that generates a command for a main air flow controller, which manipulates a main air flow valve, and an analyzer controller of proportional-integral-derivative (PID) type that generates a command for a trim air flow controller, which manipulates a trim air flow valve. The set point (ratio value) for the ratio controller is entered by an operator. The analyzer controller uses the measurements of residual $H_2S$ and $SO_2$ in a tail gas to generate a command for the trim air flow controller, so that it generates a command to bring tail gas $H_2S$-to-$SO_2$ ratio to the set point 2. This control scheme may provide a satisfactory performance of the control system if the acid gas flow is relatively steady. If the acid gas flow fluctuates (which is normally the case) it becomes very difficult to achieve a satisfactory performance of the control. As a result, in many cases a very expensive additional treatment of the tail gas aimed at removing the residual $H_2S$ and $SO_2$ may be needed to reduce emissions.

U.S. Pat. No. 3,985,864 (1976) of Lucien H. Vautrain, et al. discloses an automatic control system for a Claus sulfur plant. The flow rate of the oxygen-containing gas to a process for the oxidation of hydrogen sulfide is regulated so as to be responsive to changes in pressure in the hydrogen sulfide feedstream. In both patents, the overall ratios of oxygen to hydrogen sulfide are adjusted to maintain the desired ratio of hydrogen sulfide to oxygen feed. In carrying out stoichiometric control of the hydrogen sulfide gas stream and oxygen-containing gas stream, there are five objectives cited. These objectives are (1) maintain the quantity of oxygen below that stoichiometrically required for the oxidation of the hydrogen sulfide in order to prevent the formation of sulfates; (2) maintain the oxygen quantity as close as possible to the stoichiometry required in order to promote the highest possible efficiency of oxidizing the hydrogen sulfide-containing gas stream and to reduce the sulfur content of the gaseous effluent from the process; (3) maintain stable control of the process while achieving the above two objectives, even though the gas flow may vary; (4) maintain stable control, even though the hydrogen sulfide content of the hydrogen sulfide gas-containing stream may vary; and (5) effect stable control of the process while achieving the above four objectives, even though there is a time between the occurrence of a variation in one or both of the process feedstreams and the occurrence of the measurement of the effect of that variation on the gaseous effluent from the process. In summary, both patents disclose an automated flow control scheme to maintain the required stoichiometry of the Claus reaction.

U.S. Pat. No. RE 28,864 of Andral, et al. (with a foreign priority date, application No. 70.45812 in France) discloses process and apparatus for automated regulation of sulfur production units. The process incorporates oxidation of hydrogen sulfide, in which the flow of gas carrying oxygen into the unit is regulated so as to keep an operating parameter, based on measurement of the sulfurous compound of the residual gases, level with a reference value. It is characterized by the fact that the control signal, used to regulate the flow of gas containing oxygen at the unit inlet, is a combination of a signal based on measurements taken at the inlet, and representing the theoretical flow of this gas needed to keep the operating parameter at its reference level and another signal representing the correction needed in this flow to adjust the instantaneous value of the parameter to the reference level. The disclosed process claims better control of the sulfur unit, with increased efficiency and reduced atmospheric pollution.

U.S. Pat. No. 4,100,266 of Smith (1978) discloses an automatic control system for a Claus sulfur plant, in which control of a process is accomplished by manipulating the flow rate of a feed stream containing oxygen to a furnace in such a manner that a desired proportion of the hydrogen sulfide fed to the furnace is converted to sulfur dioxide. The flow rate of a feed stream containing hydrogen sulfide to a tail gas cleanup process is also manipulated utilizing feedforward and feedback control to maintain the hydrogen sulfide and sulfur dioxide concentrations in the gas stream from the tail gas cleanup process at acceptable levels. Some other variations of the described principle were disclosed in U.S. Pat. No. 5,965,100 of Khanmamedov (1999), and 7,754,471 of Chen (2010). The described control principle may provide a satisfactory performance of the control system if the acid gas flow to the sulfur recovery process is a relatively constant value. If the acid gas flow fluctuates (which is normally the case) it becomes very difficult to achieve a satisfactory performance of the control. As a result, in many cases a very expensive additional treatment of the tail gas aimed at removing the residual $H_2S$ and $SO_2$ is normally needed. Control performance has a significant effect on the emissions of environmentally harmful substances, which can be substantially mitigated by the disclosed adaptive ratio control.

U.S. Pat. No. 5,176,896 of Bela discloses apparatus and method for generation of control signal for Claus process optimization. It incorporates generation of a control signal for the optimization of sulfur removal in a Claus process unit that comprises oxidizing a portion of the tail gas stream exiting the Claus unit by contacting a portion of the tail gas with an oxygen-containing gas in the presence of a catalyst which oxidizes $H_2S$ to $SO_2$, measuring the temperature rise associated with the oxidation reaction, converting the measurement to an appropriate control signal, and using the signal to control the rate of air flow into the Claus unit. Canadian Pat. No. CA 1323173 to Lagas et al. discloses a process for the recovery of sulfur from a hydrogen sulfide containing gas (acid gas), which comprises oxidizing hydrogen sulfide with oxygen, and then reacting the product gas of this oxidation further by using at least two catalytic stages, in accordance with the equation: $2H_2S+SO_2=2H_2O+3/n\ S_n$. In order to improve the process and the process control, the invention is characterized in that the $H_2S$ concentration in the gas leaving the last catalytic stage is controlled to have a value ranging between 0.8 and 3% by volume by reducing the quantity of combustion or oxidation air passed to the oxidation stage and/or causing a portion of the hydrogen sulfide containing feedstock gas to bypass the oxidation stage and to be added to the gas flowing to a catalytic stage. As described, typical control of the Claus reaction includes an air-to-acid gas ratio controller that uses measurements of acid gas flow and generates a command for a main air flow controller, which in turn manipulates a main air flow valve, and an analyzer controller of proportional-integral-derivative (PID) type that uses measurements of $H_2S$ and $SO_2$ in a tail gas and generates a command for a trim air flow controller, which in turn manipulates a trim air flow valve. The main drawback of the available controls is related to possible fluctuations of acid gas flow and slow response of the tail gas concentrations to changes in a tail gas flow and air flow. If a tail gas flow changes the main air flow controller responds to this change very quickly incrementing air flow. However, the air-to-acid gas flow ratio demand is entered by an operator and is not optimal, so that the air flow increment would not fully correspond to the acid gas flow increment, and the increment of air flow will be either smaller or larger than the optimal necessary for a stoichiometric combustion. As a result, after all the reactions occur the concentrations of $H_2S$ and $SO_2$ in a tail gas will change. Yet, it will only be measured with some delay, after this reaction has already happen, which results in insufficiently high quality of control, observed as high fluctuations in a tail gas $H_2S$-to-$SO_2$ ratio. Another drawback is related to uncoordinated motion of the two air valves, so that one valve may have a command to open, thus increasing air flow, and the other valve to have the command to close, thus decreasing air flow, while in fact no change may be required in terms of total air required. This uncoordinated motion of the two air valves contributes to the deterioration of the control performance, as the valves respond to their commands not instantaneously but with some lag, which differs between the two valves. Those lags result in the deviations of the total air flow from the total air flow demand (sum of the two demands) and overall performance deterioration.

It would be desirable to calculate and use an optimal value for the air-to-acid gas ratio demand, so that any fluctuation in an acid gas flow should be immediately matched by corresponding amount of air-through the action of the ratio controller.

BRIEF SUMMARY OF THE INVENTION

The present invention improves performance of the control of the sulfur recovery process in the conditions of variable flow rate of acid gas and variable $H_2S$ concentration in acid gas by using an adaptive ratio control principle. In accordance with an embodiment of this invention, $H_2S$-to-$SO_2$ ratio fluctuations (molar amounts) in the tail gas are substantially reduced by generating the air flow demand that is calculated as a sum of the principal air flow demand and the supplemental air flow demand, where the principal air flow demand is calculated via multiplication of the acid gas flow by the optimal air-to-acid gas ratio demand value, and the supplemental air flow demand is calculated by a proportional-integral-derivative (PID) algorithm, with process variable of the PID algorithm based on measurements of molar amounts of residual $H_2S$ and $SO_2$ in the tail gas. An optimal value of the air-to-acid gas ratio demand is determined through learning (adaptation), which allows for the best possible rejection of disturbances coming to the control system in the form of acid gas flow fluctuations, while slow changes in the concentration of $H_2S$ in the acid gas are compensated for by adaptation aimed at finding a varying optimal value of the air-to-acid gas ratio, which changes with changes of $H_2S$ concentration. Through this principle, combustion of hydrogen sulfide is precisely controlled by the control system to maintain the hydrogen sulfide and sulfur dioxide concentrations in the tail gas at the desired ratio and acceptable levels to minimize the environmental pollution.

DETAILED DESCRIPTION OF THE INVENTION

Figure 1:
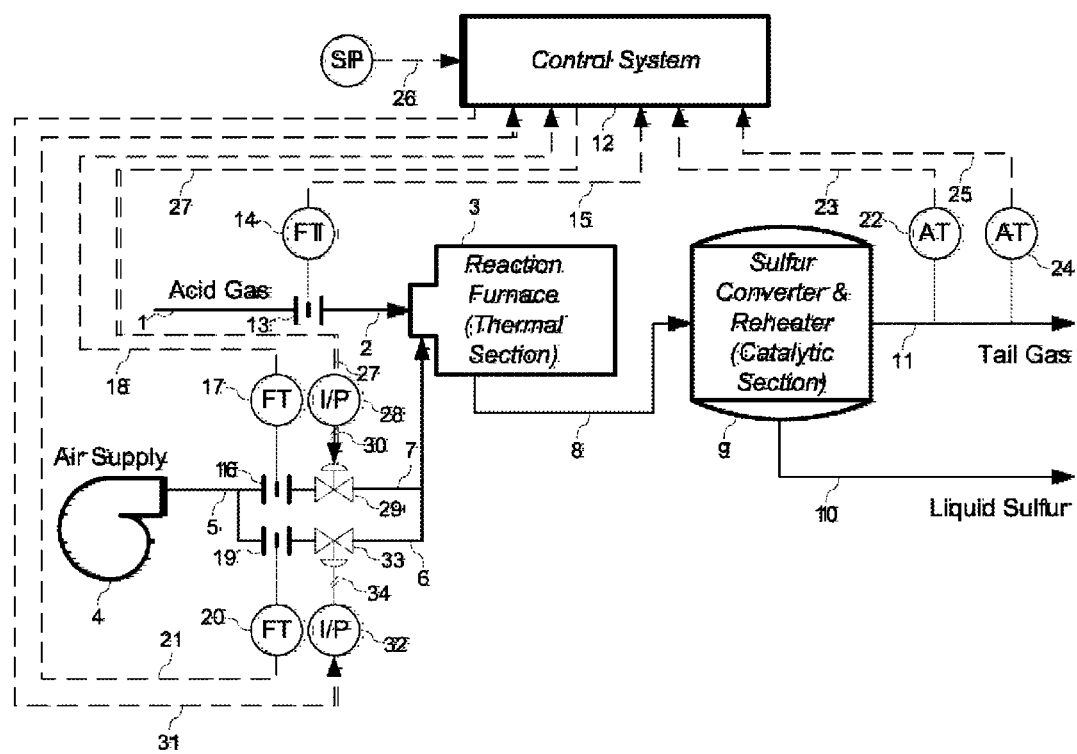
FIG. 1 is an illustration of a Claus sulfur plant with associated controls (preferred embodiment A)

The present invention relates to method and apparatus to control the ratio of air to hydrogen sulfide ($H_2S$) in the acid gas in Claus (sulfur recovery) reaction. In one specific aspect the invention relates to a method and apparatus for obtaining near optimum performance of a sulfur plant where free sulfur is produced from hydrogen sulfide. In a second specific aspect, this invention relates to a method and apparatus for reducing air pollution produced by the production of free sulfur from hydrogen sulfide. In a third specific aspect, the invention relates to a method and apparatus for controlling the ratio of hydrogen sulfide to oxygen fed to a reaction of hydrogen sulfide and oxygen to form free sulfur. In a fourth specific aspect, the invention relates to a method and apparatus for maintaining a desired hydrogen sulfide to sulfur dioxide ratio in a sulfur plant tail gas. Other possible applications of the same control principle are as follows (but not limited to those): control of fuel combustion in utility boilers by measuring $O_2$ concentration in the flue gas and manipulating the air flow on the basis of the measurements obtained; control of $SO_x$ passivation by means of ammonia injection into the gas/liquid; control of desuperheated steam temperature in utility boilers by means of spraying water into steam; control of air-fuel ratio in internal combustion engines.

Sulfur is present in natural gas principally as $H_2S$ and in other fossil fuels as sulfur-containing compounds which are converted to $H_2S$ during processing. The $H_2S$ is removed from the natural gas or refinery gas by means of one of the gas treating processes. The resulting $H_2S$-containing acid gas is processed to recover sulfur. The recovery of free sulfur from gaseous streams containing hydrogen sulfide has become a valuable procedure in the petroleum gas industries. Such an operation results in both the recovery of valuable free sulfur and a reduction of atmospheric pollution. The Claus process is widely used for sulfur recovery from $H_2S$. The Claus process as used today is a modification of a process first used in 1883 in which $H_2S$ was reacted over a catalyst with air (oxygen) to form elemental sulfur and water. A modification of the Claus process was developed in 1936 in which the overall reaction was separated into a highly exothermic combustion reaction section and a moderately exothermic catalytic reaction section in which sulfur dioxide formed in the combustion section reacts with unburned $H_2S$ to form elemental sulfur.

In practice, the control of the reaction is usually implemented with the use of measurements of the acid gas flow and the ratio of residual $H_2S$ and $SO_2$ in the tail gas after the reaction, and by means of two air valves with respective controllers (loops) that utilize the above measurements. This control scheme may provide a satisfactory performance of the control system if the acid gas flow is a relatively constant value. If the acid gas flow fluctuates (which is normally the case) it becomes very difficult to achieve a satisfactory performance of the control. As a result, in many cases a very expensive additional treatment of the tail gas aimed at removing the residual $H_2S$ and $SO_2$ is normally needed. Control performance has a significant effect on the emissions of environmentally harmful substances, and therefore, development of process model suitable for controller design and tuning may have a high environmental impact.

In many aspects the Claus process is no different than a regular combustion process of the fuel gas in utility boilers, for example. However, very strict requirements to the residual $H_2S$ and $SO_2$ make the control of the Claus reaction a much more difficult problem. Unlike the conventional combustion process, which allows for the use of different air-to-fuel ratios, the Claus reaction requires the stoichiometric values of $H_2S$ and air. Commonly, the residual $H_2S$ is further burned and converted into environmentally less harmful $SO_2$ and the latter is emitted into the atmosphere. For that reason, excess of either $H_2S$ or $SO_2$ compared to the stoichiometric values increases emissions, and only optimal $H_2S$ to $SO_2$ ratio (corresponding to stoichiometric combustion) provides minimal $SO_2$ emissions. Another difference that complicates the control of the Claus reaction is uncontrolled acid gas flow (all available acid gas must be incinerated) versus regulated fuel flow in other types of combustion. The main objective of the control quality enhancement is to ensure the conversion of all available $H_2S$ into relatively neutral and environmentally safe sulfur; increase of sulfur production is usually a secondary objective only.

The free sulfur generally is produced by a process which involves the following two reactions. The reaction in the thermal or combustion reaction section is given by the following expression (J. B. Pfeiffer, *Sulfur Removal and Recovery from Industrial Processes*, Washington, D.C., U.S.A., American Chemical Society, 1975):

$$H_2S + 1\tfrac{1}{2}O_2 \rightarrow SO_2 + H_2O \qquad (1)$$

The reaction in the combustion and catalytic reaction sections is given as follows:

$$2H_2S + SO_2 \rightarrow 3/xS_x + 2H_2O \qquad (2)$$

If high $H_2S/SO_2$ conversion levels are to be reached in the Claus reaction, this ratio should be kept as close as possible to the stoichiometric value of two.

The first reaction generally takes place in the combustion chamber of a boiler. Since this reaction is highly exothermic, the substantial amount of heat which is released is recovered in the form of steam production. One third of the source hydrogen sulfide is combined with air to form sulfur dioxide in this reaction. The reaction of the hydrogen sulfide is combined with the reaction products from the combustion chamber to carry out the second reaction in the furnace. The effluent from the furnace is cooled, and the free sulfur product is recovered as a liquid.

All the hydrogen sulfide and sulfur dioxide gases will not be converted in the furnace. The remaining unconverted gases are passed through a catalytic sulfur removal reactor to further convert the unreacted hydrogen sulfide and sulfur dioxide to free sulfur. The effluent from the reactor is cooled, and the free sulfur product is removed as a liquid.

Let $q_{H2S}$ be the molar amount (flow) of $H_2S$ and $q_{O2}$ be the molar amount (flow) of $O_2$. Then assuming that all oxygen is reacted in the combustion reaction we can write an expression for the molar amount of $SO_2$ obtained as a result:

$$q^{(1)}{}_{SO2}=\tfrac{2}{3}q_{O2} \tag{3}$$

where superscript "1" refers to the combustion reaction. In this reaction the amount of $H_2S$ equal to ⅔ of the amount of the oxygen is consumed, and the remaining $H_2S$ is:

$$q^{(1)}{}_{H2S}=q_{H2S}-\tfrac{2}{3}q_{O2} \tag{4}$$

In the combustion and catalytic reaction section, not all available $H_2S$ and $SO_2$ react but only a certain amount. We describe the percentage of $H_2S$ and $SO_2$, reacted in the catalytic reaction section, with respect to the stoichiometric amounts of $H_2S$ and $SO_2$, by the sulfur recovery factor $k_r$. The value of the sulfur recovery factor would, therefore, normally be slightly below 1. The remaining amounts of $H_2S$ and $SO_2$ after the catalytic section would be as follows:

$$q^{(2)}{}_{H2S}=(1-k_r)q^{(1)}{}_{H2S} \text{ and } q^{(2)}{}_{SO2}=q^{(1)}{}_{SO2}-0.5k_r q^{(1)}{}_{H2S} \text{ if } q^{(2)}{}_{H2S}<=2q^{(1)}{}_{SO2} \tag{5}$$

where superscript "2" refers to the catalytic reaction or $$q^{(2)}{}_{H2S}=q^{(1)}{}_{H2S}-2k_r q^{(1)}{}_{SO2} \text{ and } q^{(2)}{}_{SO2}=(1-k_r)q^{(1)}{}_{SO2} \text{ if } q^{(2)}{}_{H2S}>2q^{(1)}{}_{SO2} \tag{6}$$

Usually the control utilizes the ratio of the two values, which shows how far the amounts of the reagents are from the stoichiometric values:

$$\rho=q^{(2)}{}_{H2S}/q^{(2)}{}_{SO2} \tag{7}$$

Considering oxygen content in the air of 21% the air flow $q_{air}$ is related to the oxygen flow as follows:

$$q_{O2}=0.21 q_{air} \tag{8}$$

From the above formulas, we can obtain the relationship between the air/$H_2S$ ratio r at the process input and $H_2S/SO_2$ ratio in the tail gas p as follows (I. Boiko, "Dynamical model of the Claus process and its identification," *Proc. 2007 American Control Conference*, New York, USA, pp. 2260-2264):

$$\rho = \frac{1-0.14r-0.28r k_r}{0.14r(1-k_r)} \text{ at } H_2 \tag{9}$$

S excess(compared to stoichiometric value), $$\rho = \frac{(1-k_r)(1-0.14r)}{0.14r-0.5k_r(1-0.14r)} \text{ at } \tag{10}$$

air excess (compared to stoichiometric value)

In the past, the noncondensed material from the catalytic sulfur removal reactor (tail gas) was simply passed to as incinerator. Recently various processes have been developed to clean up the tail gas from the catalytic sulfur removal reactor, resulting in less air pollution and in additional free sulfur recovery. When a tail gas cleanup process is utilized, close control of the desired ratios between the gases to be reacted also must be maintained. Sometimes it is also desirable to be able to change the ratio of the hydrogen sulfide and the sulfur dioxide in the tail gas to conserve the catalyst in the tail gas cleanup process.

The main idea of the present invention is to use an adaptive ratio control principle that is first introduced in the present invention. The use of this principle is based on the supposition that there are two main types of disturbances that come to the control system for this process: the acid gas flow fluctuations and the acid gas composition (mainly $H_2S$ concentration). This supposition totally agrees with the practice of sulfur recovery control. The adaptive part of the adaptive ratio control is aimed at determination of the optimal value of the necessary air-to-acid gas ratio (ratio ser point), so that when an acid gas fluctuation occurs an equivalent increment or decrement of air flow demand is calculated immediately by the ratio controller (through multiplication of the actual acid gas flow by the ratio set point). If the ratio set point is not optimal then there always exists an unmatched portion in the acid gas flow fluctuation, and proper proportion between air and acid gas will be disturbed, which in turn will results in improper proportion between $H_2S$ and $SO_2$ in the tail gas. On the other hand, the optimal value of the necessary air-to-acid gas ratio is not constant and depends on the acid gas composition. However, at relatively slow changes of the composition the optimal value of the necessary air-to-acid gas ratio (ratio set point) can be successfully determined through adaptation (learning), which is done with involvement of proper low-pass filtering of the actual air-to-acid gas ratio and additional inhibiting/permissive and nonlinear logic.

Accordingly, it is an objective of this invention to provide a method and apparatus for controlling the production of free sulfur from hydrogen sulfide. A second objective of this invention is to provide a method and apparatus for obtaining near optimum performance of a sulfur plant where free sulfur is produced from hydrogen sulfide. A third objective of this invention is to provide a method and apparatus for reducing air pollution produced by the sulfur plant. A fourth objective of this invention is to provide a method and apparatus for maintaining a desired hydrogen sulfide to sulfur dioxide ratio in a tail gas.

In accordance with the present invention, an improved method and apparatus for controlling the production of free sulfur from hydrogen sulfide is provided wherein a processor-based control system means (distributed control system or programmable logic controller, for example) is utilized to obtain near optimum performance from a sulfur plant by maintaining the $H_2S/SO_2$ ratios in the tail gas at desired value. The desired $H_2S/SO_2$ ratio in the tail gas is maintained at a desired value by controlling the air flow to the furnace in such a manner that enough $H_2S$ in the acid gas feed is converted to $SO_2$ to give the desired $H_2S/SO_2$ ratio in the gas stream flowing from the furnace to the catalytic sulfur removal reactors.

For the sake of simplicity, the invention is illustrated and described in terms of a sulfur plant wherein the catalytic sulfur converters are Claus converters.

Although the invention is illustrated and described in terms of a specific embodiment, the applicability of the use of the invention described herein extends to sulfur plants using different types of catalytic sulfur converters.

Controllers shown may utilize the various modes of control such as proportional (P), proportional-integral (PI), proportional-derivative (PD), or proportional-integral-derivative (PID). In a preferred embodiment proportional-integral-derivative controllers are utilized. All other variations of the PID controller can be obtained from the PID controller by setting respective gains to zero. The operation of these types of controllers is well known in the art. The output control signal of a proportional-integral-derivative controller may be represented as $$u(t) = K_p e(t) + K_i \int_0^t e(t)\,dt + K_d \frac{de(t)}{dt}$$

where
t is time,
u is output control signal;
e is difference between two input signals (error),
and $K_p$, $K_i$ and $K_d$ are proportional gain, integral gain and derivative gain, respectively.

Referring now to the drawings and in particular to FIG. 1, which illustrates a preferred embodiment that involves two (main and trim) air control valves (preferred embodiment A), an acid-gas feed stream containing $H_2S$ passes from supply conduit means 1 through conduit means 2 into the reaction furnace 3. The reaction furnace 3 is also supplied with air from supply 4 through air conduit means 5. In another embodiment, the reaction furnace 3 is supplied with air from supply 4 through air conduit means 5, primary air supply conduit means 6 and trim air conduit means 7. Sufficient air is mixed with the acid-gas feed in the furnace to convert one-third of the $H_2S$ fed to the furnace to $SO_2$ and also burn any hydrocarbons present in the acid-gas feed. The well-known stoichiometric reaction in the furnace is given by formula (1). Burning of one-third of the $H_2S$ to $SO_2$ yields a desired $H_2S/SO_2$ mol ratio of 2.0 in the reaction effluent gas which leaves the reaction furnace 3 via conduit means 8.

The flame temperature in the reaction furnace may reach temperatures of 2450° F. At such temperature some of the unburned $H_2S$ can react with the $SO_2$ formed by the reaction given in equation (1), to form free sulfur vapor in accordance with the reaction of equation (2). This will decrease the temperature of the hot gases to about 2300° F. Heat can be removed from the hot gases by heat exchange with water passed through the reaction furnace 3. The hot gases in the reaction furnace are typically cooled to 550° F. before exiting the furnace.

The hot gases pass from the reaction furnace 3 through conduit means 8 to a catalytic section 9, which comprises a series of reactors, reheaters and condensers. The free sulfur vapor formed in the reaction furnace 9 is condensed in the condensers and the resulting liquid sulfur can then be separated from the main gas stream containing unreacted $H_2S$ and $SO_2$. The separated liquid free sulfur flows through conduit means 10 to sulfur collection and storage means.

The Claus reaction proceeds to a further degree of completion in the presence of the Claus catalyst in the Claus catalytic converters contained in the catalytic section 9. The reaction involved is given by formula (2). The gas stream which now contains free sulfur plus the unreacted $H_2S$ and $SO_2$ flows out of the Claus catalytic converter to sulfur condenser where the free sulfur is condensed. The condensed free sulfur flows through conduit means 10 to sulfur collection and storage means.

The Claus tail gas, containing the remaining unreacted $H_2S$ and $SO_2$ which are still in a $H_2S/SO_2$ mol ratio of about 2.0, flows through conduit means 11 to further processing (cleaning) or is released to the atmosphere.

It is desirable to have an $H_2S/SO_2$ mol ratio of slightly greater than 2.0 if the tail gas is further processed.

As has been stated, one object of this invention is to optimize the performance of a sulfur plant by maintaining the $H_2S/SO_2$ ratio to the sulfur removal reactors at least substantially at 2.0.

The $H_2S/SO_2$ mol ratio to the catalytic section 9 can be maintained by manipulating the flow of air through conduit 5 to the reaction furnace 3.

Control of the process is accomplished by providing processor-based control system means 12 with measured process variables as inputs. These process variables are then utilized by processor-based control system means 12 to generate signals to the valves which are used to maintain the various controlled flow rates at desired levels.

The following sensors (transmitters) are used by the processor-based control system means 12 to measure the process variables. Flow sensor 13, located in supply conduit means 2, measures the actual flow rate of acid gas through conduit means 2 to furnace 3. Flow transducer 14, associated with flow sensor 13, transmits this information to control system means 12 via data signal 15. Flow sensor 16, located in the primary air supply conduit means 6, measures the actual flow rate of air through conduit means 6. Flow transducer 17, associated with flow sensor 16, transmits this information to control system means 12 via data signal 18. Flow sensor 19, located in trim air conduit means 7, measures the actual flow rate of the trim air. Flow transducer 20, associated with flow sensor 19, transmits this information to control system means 12 via data signal 21.

An analyzer 22, such as a gas chromatograph, analyzes the Claus tail gas flowing from the catalytic section 9 through conduit means 11. Analyzer 22 provides the control system means 12 with data signal 23 which is representative of the $H_2S$ concentration in the tail gas. An analyzer 24, such as a gas chromatograph, analyzes the Claus tail gas flowing from the catalytic section 9 through conduit means 11. Analyzer 24 provides the control system means 12 with data signal 25 which is representative of the $SO_2$ concentration in the tail gas. Optionally, both measurements: the $H_2S$ concentration and the $SO_2$ concentration in the tail gas can be performed by one analyzer (chromatograph).

Control system means 12 is also supplied with certain $H_2S/SO_2$ ratio setpoint value through setpoint entry means 59 (operator entry or coding). Signal 26 is representative of the required $H_2S/SO_2$ ratio in the tail gas stream and has a value of 2.0 in this preferred embodiment.

Based on the described input data, control system means 12 calculates the required flow rate of the main air and trim air. Signal 31, representative of the required flow rate of the trim air, is supplied to the current to pneumatic transducer 32. Control valve 33 is manipulated in response to signal 34 to provide the desired trim air flow rate. Signal 27, representative of the required flow rate of the main air, is supplied to the current to pneumatic transducer 28. Control valve 29 is manipulated in response to signal 30 to provide the desired main air flow rate. It should be noted that main air flow 18 and trim air flow 21 are not the same flows as principal air and supplemental air, which are parts of the calculation of the total air flow demand. Moreover, supplemental air can be positive, zero or negative value, while main air and trim air are always positive values. However, the sum of main air and the trim air is supposed to be equal to the total air demand, which in turn is the sum of principal air demand and the supplemental air demand. Therefore, ideally (when both main air and trim air are equal to the set points for respective air flow controllers) the sum of main air and the trim air is equal to the sum of principal air and supplemental air demands.

In the preferred embodiment that involves one air control valve (preferred embodiment B) the following elements of the diagram are not present: as numbered by 19, 20, 21, 31, 32, 33, and 34.

Figure 2:
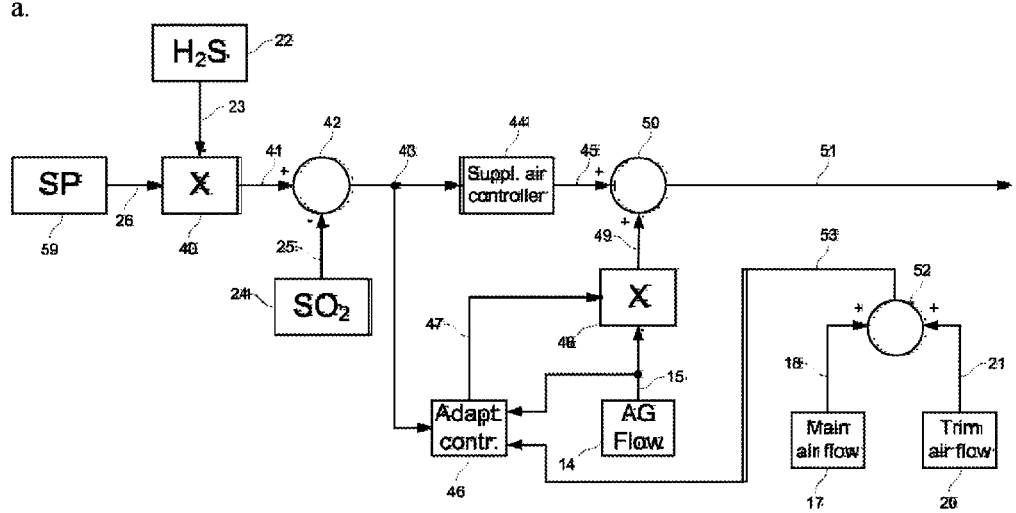
FIG. 2 is a schematic of a processor-based control system means for the calculation of the principal air flow demand, supplemental air flow demand and total air flow demand ((a)—preferred embodiment A, (b)—preferred embodiment B)
Figure 2:
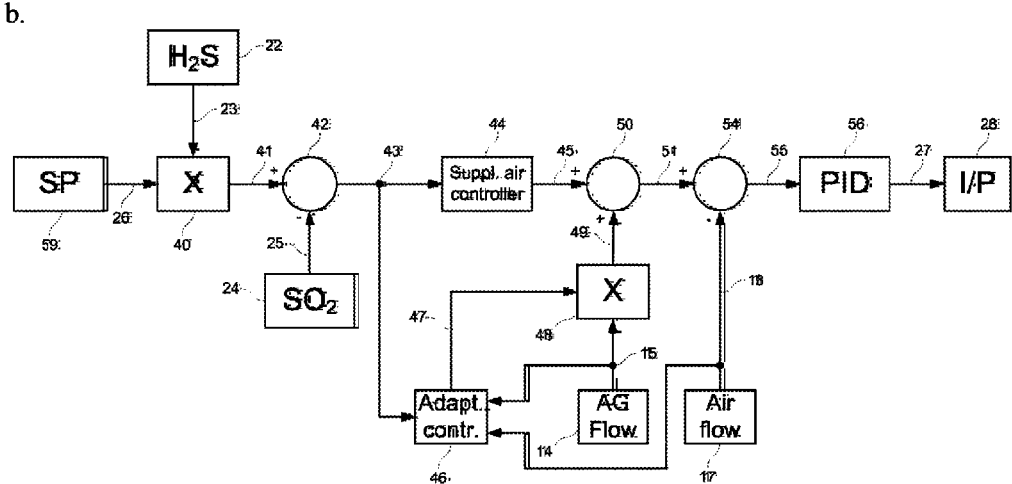

FIG. 2 illustrates a part of the control system, in which calculations of the total air demand for the air flow controller(s) are done. In the preferred embodiments it is realized through a software module in the processor-based control system. The method and apparatus shown in FIG. 2 is only one of many such configurations which could be utilized to perform the required calculations. It should also be recognized that a processor-based control system could easily be programmed to perform the required calculations.

Signal 23, representative of the actual $H_2S$ concentration in the tail gas measured by analyzer 22, is provided to multiplying means 40. Multiplying means 40 is also provided with set point signal 26, representative of the required $H_2S/SO_2$ ratio in the tail gas. Signal 23 is multiplied by signal 26 to produce signal 41. Signal 25, representative of the actual $SO_2$ concentration in the tail gas measured by analyzer 24, is provided to summing means 42. Signal 41 is summed with negative signal 25 to produce signal 43, which is supplied to controller 44. In a preferred embodiment, controller 44 is a proportional-integral-derivative controller. However, controller 44 can be a relay controller or a different type of controller, for example a relay type of controller well-known in the art (I. Boiko, *Discontinuous Control Systems: Frequency-Domain Analysis and Design*, Boston, Birkhauser, 2009). The output signal 45 of such a controller is well known in the art, as has been previously stated. Signal 45 is the supplemental air demand. It can be a positive, zero or negative quantity. It is supplied to summing means 50. Signal 43 is also supplied to an adaptive controller 46. Signal 15, representative of the actual acid gas flow measured by flow transducer 14, is provided to the adaptive controller 46.

In the preferred embodiment that involves two (main and trim) air control valves (preferred embodiment A; as illustrated by FIG. 2a), signal 18, representative of the actual main air flow measured by the flow transducer 17, is provided to a summing means 52. Signal 21, representative of the actual trim air flow measured by the flow transducer 20, is provided to a summing means 52 too. Signals 18 and 21 are summed together producing the output signal 53, which is the actual total air flow representative. Signal 53 is supplied to the adaptive controller 46. The output signal 47 of the adaptive controller 46 is produced as per the algorithm that is described below. Signal 47 is supplied to multiplying means 48. Signal 15, representative of the actual acid gas flow, is also supplied to multiplying means 48. The output signal 49 of the multiplying means 48 is the principal air demand. It is supplied to the summing means 50. The output signal 51 of the summing means 50 is the total air demand. It is supplied to a part of the control system means for the calculation of commands to main air control valve and trim air control valve as illustrated by FIG. 3 and described below, which in the preferred embodiment A is a combination of two proportional-integral-derivative controllers.

In the preferred embodiment that involves one air control valve (preferred embodiment B; as illustrated by FIG. 2b), signal 18, representative of the actual air flow measured by flow transducer 17, is provided to the adaptive controller 46. Signal 18 is also supplied with the negative sign to a summing means 54. The output signal 47 of the adaptive controller 46 is produced as per the algorithm that is described below. Signal 47 is supplied to multiplying means 48. Signal 15, representative of the actual acid gas flow, is also supplied to multiplying means 48. The output signal 49 of the multiplying means 48 is the principal air demand. It is supplied to the summing means 50. The output signal 51 of the summing means 50 is the total air demand. It is supplied to a summing means 54. The output signal 55 of the summing means 54 is supplied to an air flow controller 56. In a preferred embodiment B, controller 56 is a proportional-integral-derivative controller. The output signal 27 of the controller 56 is provided to the current-to-pneumatic transducer 28 described above (see FIG. 1).

Figure 3:
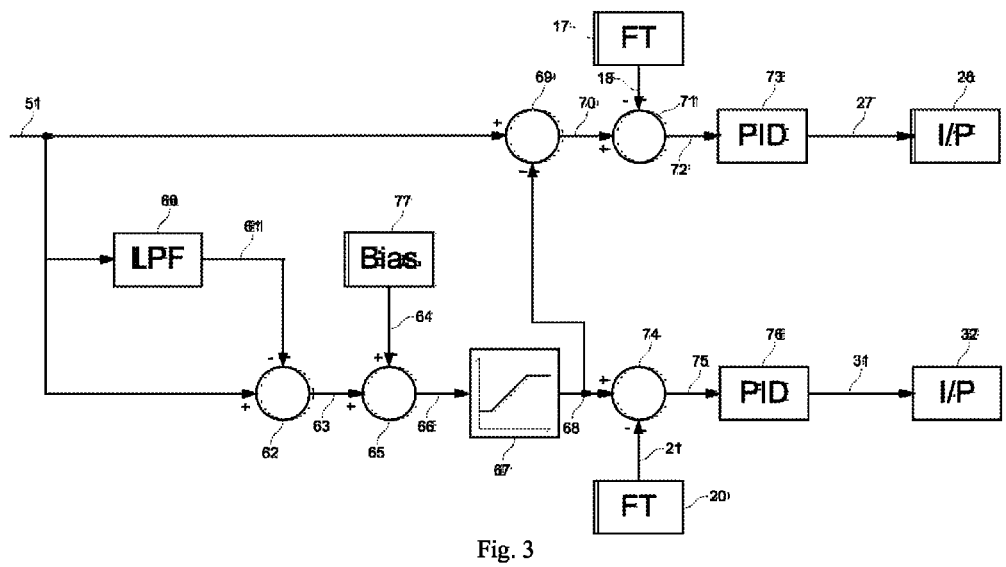
FIG. 3 is a schematic of a processor-based control system means for the calculation of commands to main air control valve and trim air control valve for preferred embodiment A.

FIG. 3 illustrates a preferred embodiment that involves two (main and trim) air control valves (preferred embodiment A) of an air flow controller, which is realized as a software module in the processor-based control system. It should also be recognized that a processor-based control system could easily be programmed to perform the required calculations.

The total air demand signal 51 is supplied to a low-pass filter 60, to a summing means 62, and to a summing means 69. The low-pass filter 60 performs low-pass filtering of signal 51 in accordance with the transfer function of the filter and provides an output signal 61. In a preferred embodiment, the transfer function of the filter is $W_{LPF1}(s)=1/[(T_1s+1)(T_2s+1)]$ where $T_1$ and $T_2$ are the time constants, s is the Laplace variable. Transfer function means of description of a filter is well known in the art. Output signal 61 with negative sign is supplied to a summing means 62, which produces the output signal 63. Signal 63 is the difference between the total air demand and low-pass filtered total air demand signal and, therefore, contains the fast component of the total air demand. Signal 63 is supplied to a summing means 65. Constant bias signal 64 generated with the use of biasing means 77 within the air flow controller is supplied to the second input of the summing means 65. The constant bias signal value 64 is selected in such a way that it approximately corresponds to the trim air flow at the 50% opening position of the trim air flow valve, so that in average the trim air flow valve will travel around 50% opening (which usually represents a linear part of the air flow control characteristic). If necessary, the constant bias value can be adjusted to ensure optimal travel range of the trim air valve. Output signal 66 of the summing means 65 is supplied to a limiter 67, which limits the signal 66 from below and above producing the output signal 68, which is the set point for the trim air flow controller. Signal 66 is limited from below by a certain non-negative value to prevent the set point for the trim air flow controller to be a negative value or a too small positive value, when the trim air valve has to go to nearly closed position to provide the required air flow. Signal 66 is also limited from above by a certain positive value to prevent the set point for the trim air flow controller to be a too high value, when the trim air valve has to go to nearly open position to provide the required air flow or the air flow goes to saturation. The trim air flow set point 68 is supplied with the negative sign to a summing means 69 that provides the output signal 70, which is the set point for the main air flow controller. The set point for the main air flow controller is, therefore, produced as the difference between the total air demand 51 and the trim air flow controller set point 68. Thus the sum of the set points for the main air flow controller and the trim air flow controller is always equal to the total air flow demand. This system allows the faster trim air adjustment to prevail over the shorter term with the main air controls prevailing over the longer term.

Signal 70 is supplied to a summing means 71, and signal 18, which is a representative of the main air flow, is supplied with the negative sign to the second input of the summing means 71, producing the difference between the main air flow controller set point and the actual main air flow. The output 72 of the summing means 71 is supplied to a main air flow controller 73. Controller 73 is a proportional-integral controller in a preferred embodiment. The output 27 of the controller is supplied to the current-to-pneumatic transducer (see FIG. 1).

Set point 68 for the trim air flow controller is supplied to a summing means 74, and signal 21, which is a representative of the trim air flow, is supplied with the negative sign to the second input of the summing means 74, producing the difference between the trim air flow controller set point and the actual trim air flow. The output 75 of the summing means 74 is supplied to a trim air flow controller 76. Controller 76 is a proportional-integral controller in a preferred embodiment. The output 31 of the controller is supplied to the current-to-pneumatic transducer (see FIG. 1).

Figure 4:
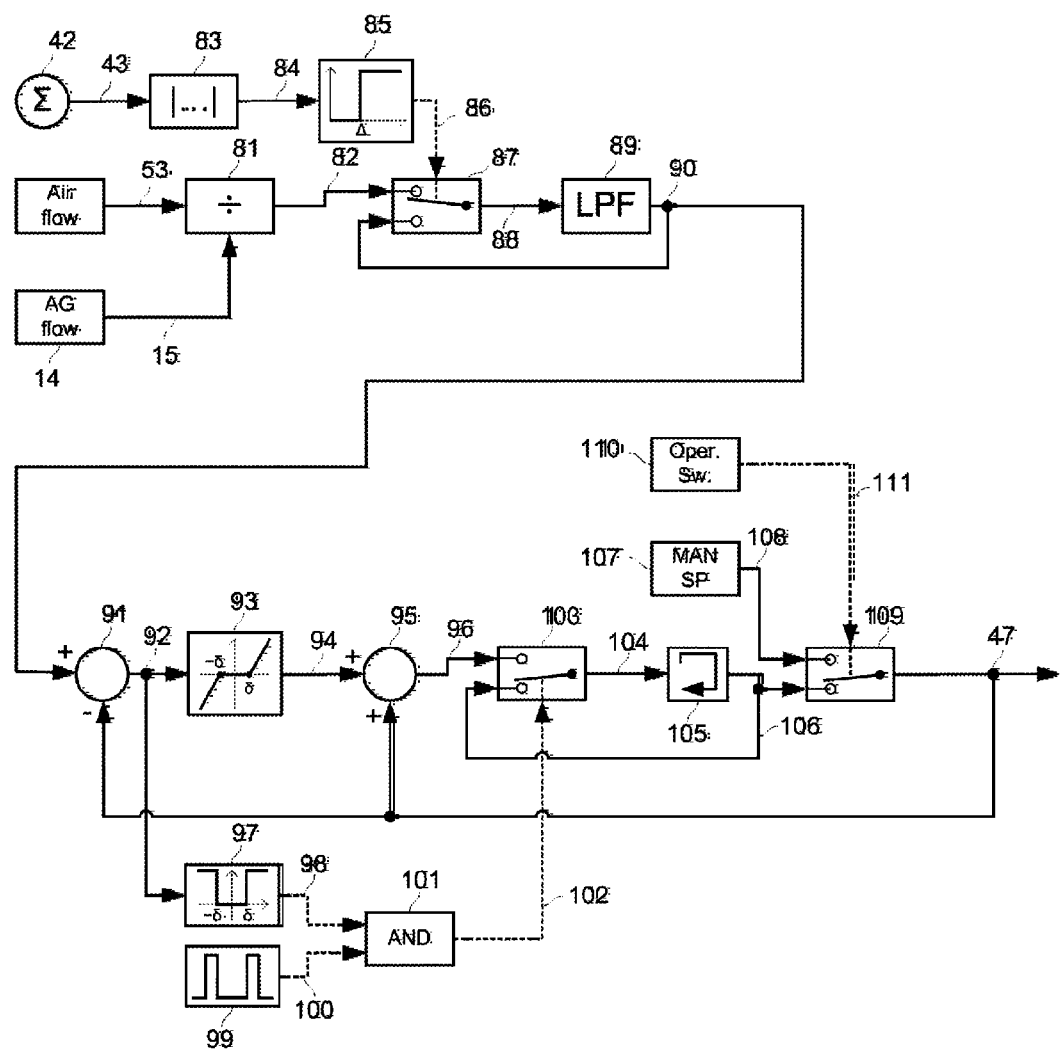
FIG. 4 is a schematic of a processor-based control system means of the adaptive control (preferred embodiments A and B)

FIG. 4 illustrates a preferred embodiment of an adaptive controller, which in the preferred embodiment is a software module in the processor-based control system. It should also be recognized that a processor-based control system could easily be programmed to perform the required calculations.

The objective of the adaptive controller is to provide the control system with an optimal value of the required air-to-acid gas ratio (ratio set point). The adaptation (learning) is carried out through low-pass filtering of the actual air-to-acid gas ratio subject to the permissive signal provided by an additional logic that uses $H_2S/SO_2$ ratio in the tail gas as a signal witnessing proper air-to-acid gas ratio.

The total actual air flow signal 53 either measured by the flow transducer 17 (for the preferred embodiment B) or obtained by the summation of the main air flow signal 18 and trim air flow signal 21 (for the preferred embodiment A; see also FIG. 1 and FIG. 2) is supplied to the dividing means 81. The actual acid gas flow signal 15 measured by the acid gas flow transducer 14 (see also FIG. 1 and FIG. 2) is supplied to the second input of the dividing means 81. The dividing means 81 perform the division of signal 18 by signal 15 producing the output 82. Signal 82 is supplied to the first input of the selector 87, which produces the output signal 88 as a result of the selection between signals supplied to the first and the second inputs. Signal 88 is supplied to a low-pass filter 89. The low-pass filter 89 is used for the determination of the actual averaged (on a relatively long period of time suitable for learning) air-to-acid gas ratio, subject to the condition of the closeness to optimal $H_2S$-to-$SO_2$ ratio in the tail gas. The low-pass filter 89 performs low-pass filtering of signal 88 in accordance with the transfer function of the filter and provides an output signal 90. In both preferred embodiments, the transfer function of the filter is $W_{LPF2}(s)=1/[(T_3s+1)(T_4s+1)]$, where $T_3$ and $T_4$ are the time constants, s is the Laplace variable. Transfer function means of description of a filter is well known in the art. Time constants $T_3$ and $T_4$ of the low-pass filter should be selected large enough, so that the filter is capable of filtering out fluctuations of air-to-acid gas flow caused by the action of the controller 44. But these time constants should not be too large, so that the adaptive controller could adjust the air-to-acid gas ratio set point 47 quickly enough to changes in the concentration of $H_2S$ in the acid gas. Signal 90 is supplied to the second input of selector 87. The signal 43 produced by the summing means 42 (see also FIG. 2) is supplied to a means for computing the absolute value 83, which in turn produces an output signal 84. Signal 84 is supplied to a compactor 85, which compares the input to the threshold value producing a logical (Boolean) output signal 86 in dependence on the results of this comparison. If the input signal 84 is greater than or equal to the threshold value $\Delta$ then the output signal 86 is 1, if the input signal 84 is smaller than the threshold value $\Delta$ then the output signal 86 is 0. Logical signal 86 is supplied to the control input of the selector 87. Selector 87 produces the output signal 88 according to the following algorithm: if signal 86 is equal to 0 then the first input (signal 82) is selected, if signal 86 is equal to 1 then the second input (signal 90) is selected. The signal selection provided by the selector 87 and associated logic is intended for the purpose of learning (adaptation), so that only acceptable values of air-to-acid gas ratio, which is witnessed by signal 43 being within assigned limits, are processed by the low-pass-filter 89.

The output signal 90 of the low-pass filter is supplied to a summing means 91. The output of the adaptive controller (which is the air-to-acid gas ratio set point) 47 is supplied with the negative sign to the second input of the summing means 91. The summing means 91 produces the output signal 92, which is the difference between signal 90 and signal 47. Signal 92 is supplied to a nonlinear block 93, which produces an output signal 94 in accordance with the following equation:

$$x_{94} = \begin{cases} x_{92} - \delta & \text{if } x_{92} > \delta \\ 0 & \text{if } -\delta \leq x_{92} \leq \delta \\ x_{92} + \delta & \text{if } x_{92} < -\delta \end{cases}$$

where $x_{92}$ is signal 92, $x_{94}$ is signal 94, $\delta$ is a positive quantity (air-to-acid gas ratio update tolerance). Nonlinear block 93 is introduced with the purpose to increase stability of the adaptive ratio control through the introduction of the deadband nonlinearity, so that no adaptation happens if the error signal 92 is within the dead band. This slightly reduces the accuracy of the adaptive ratio control (because small nonzero errors in the air-to-acid gas ratio are allowed) but improves the stability via elimination of interactions between the adaptive ratio control and the proportional-integral-derivative control.

Signal 92 is also supplied to a comparator 97, which compares the input to the threshold value $\delta$ (air-to-acid gas ratio update tolerance) producing a logical (Boolean) output signal 98 in dependence on the results of this comparison. If the input signal 92 is greater than the threshold value $\delta$ or input signal 92 is smaller than the negative threshold value $-\delta$ then the output signal 98 is 1, if the input signal 92 is within the range $[-\delta; \delta]$ then the output signal 98 is 0. Logical signal 98 is supplied to a logical AND block 101. The system has means of sampling 99. Means of sampling 99 produces logical (Boolean) signal 100, which is short pulses of predefined frequency that can be equal to or lower than the frequency of the algorithm execution in the control system. Output signal 100 of the sampling means is supplied to the logical AND block 101. Logical AND block 101 produces logical (Boolean) output signal in accordance with the following logic. If both input signals 98 and 100 are 1 then the output signal 102 is 1; all other combinations of the input signals produce the output signal 102 value of 0. Signal 102 is supplied to the control input of a selector 103.

Output signal 94 of the nonlinear block 93 is supplied to the summing means 95. The output of the adaptive controller (which is the air-to-acid gas ratio set point) 47 is supplied to the second input of the summing means 95. Summing means 95 produces an output signal 96, which is the sum of signal 47 and signal 94. Output signal 96 is supplied to the second input of the selector 103. Selector 103 produces the output signal 104 according to the following algorithm: if signal 102 is equal to 0 then the first input (signal 106) is selected, if signal 102 is equal to 1 then the second input (signal 96) is selected. Signal 104 is supplied to a memory block 105, which stores the value until another input value (signal 104) comes and produces an output signal 106. The values stored in the memory block are updated with the frequency generated by the sampling means 99, subject to the logical 1 value of signal 98. Signal 98 serves as a permissive to update a value in the memory block 105. This value is, therefore, updated only if the difference between the output of the low-pass filter 89 and the current the air-to-acid gas ratio set point 47 is large enough (larger than $\delta$). Output signal 106 is supplied to the first input of a selector 109.

The system comprises a means of entry of a manual air-to-acid gas ratio set point 107, with the output signal representative of the manual set point 108. Manual set point can be used primarily for the start-up of the system, when learning through low-pass filtering using filter 89 is not yet done. Output signal 108 is supplied to the second input of a selector 109. The system comprises an operator switch 110 allowing the operator to select between the manual (with a manual air-to-acid gas ratio set point) or automatic (with the air-to-acid gas ratio set point produced automatically through adaptation) modes of operation. If the selected mode is "automatic" the switch 110 produces a logical (Boolean) output signal 111 of 0; if the selected mode is "manual" the switch 110 produces a logical (Boolean) output signal 111 of 1. Selector 109 produces the output signal 47 according to the following algorithm: if signal 111 is equal to 0 then the first input (signal 106) is selected, if signal 111 is equal to 1 then the second input (signal 108) is selected. Output signal 47 of the selector 109 is the output signal of the whole adaptive controller.

In FIG. 4, selectors 87, 103 and 109 are shown in the position corresponding to the control signal 86, 102 and 111 (respectively) equal to zero.

The invention has been described in terms of a presently preferred embodiment as shown in FIG. 1, FIG. 2, FIG. 3, and FIG. 4. Specific components which can be used in the practice of the invention as shown in FIG. 1 are as follows:

In the preferred embodiment, analyzer 22 and 24 is Ametek 880-NSL; flow sensors 13, 16, and 19 and associated transducers 14, 17, and 20; control valves 29, and 33, and current to pressure transducers 28, and 32 are each well known, commercially available control components such as are described at length in Béla G. Lipták, INSTRUMENT ENGINEERS' HANDBOOK, 4th Edition, Vol. 1 and 2, CRC Press, 2003.

While the invention has been described in terms of the presently preferred embodiment, reasonable variations and modifications are possible, by those skilled in the art, within the scope of the described invention and the appended claims.

I claim:

1. For a sulfur recovery plant, comprising a furnace (3), first conduit (1) for passing a first feed stream of acid gas containing hydrogen sulfide H2S into said furnace, second conduit (5) for passing a second feed stream of air into said furnace to convert part of the H2S contained in the first feed stream to sulfur dioxide SO2, third conduit (8) for withdrawing the resulting gaseous reaction mixture, containing free sulfur and unreacted H2S and SO2 gases, from said furnace, a catalytic sulfur converter means (9) to convert a portion of the unreacted H2S and SO2 gases contained in said gaseous reaction mixture to free sulfur, a sulfur removal apparatus to remove the free sulfur from the resulting gaseous reaction mixture produced in said catalytic sulfur converter thereby producing a tail gas stream containing unreacted H2S and SO2;

an apparatus comprising
a first flow sensor (13) for establishing a first signal representative (15) of an actual flow rate of said first feed stream flowing through said first conduit;
a second flow sensor system, which is comprised of two flow sensors (16), (19), for establishing a second signal representative of an actual flow rate of said second feed stream flowing through said second conduit;
a first analyzer (22) for establishing a third signal representative (23) of the H2S concentration in said tail gas stream;
a second analyzer (24) for establishing a fourth signal representative (25) of the SO2 concentration in said tail gas stream;
a set point entry module for establishing a fifth signal representative (26) of a required ratio of H2S concentration in said tail gas stream to SO2 concentration in said tail gas stream through operator entry or programming a default value of 2;
a first computation module for establishing a sixth signal representative (43) through multiplication of said third signal representative by said fifth signal representative and subtracting from this product said fourth signal representative;
a second computation module for establishing a principal air flow demand signal (49);
a third computation module for establishing a supplemental air flow demand signal (45), where supplemental air flow demand can be positive, zero or negative quantity;
a fourth computation module for establishing a total air flow demand signal (51) through summation of said principal air flow demand signal (49) and said supplemental air flow demand signal (45);
and valve system for manipulating the flow rate of said second feed stream of air in response to said total air flow demand signal (51).

2. Apparatus in accordance with claim 1 wherein said valve system for manipulating the flow rate of said second feed stream of air in response to said total air flow demand signal further comprises
a first proportional-integral-derivative air controller (56), which compares said total air flow demand signal (51) and second signal representative (18) producing a seventh signal representative (27);
an actuated valve (29) for manipulating the flow rate of said second feed stream of air in response to said seventh signal representative (27).

3. Apparatus in accordance with claim 1 wherein said valve system for manipulating the flow rate of said second feed stream of air in response to said total air flow demand signal further comprises
a first low-pass filter (60) producing an output signal (61) in response to said total air flow demand signal (51) in accordance with the transfer function of a low-pass filter, which in a preferred embodiment is
$W_{LPF1}(s)=1/[(T_{1s}+1)(T_{2s}+1)]$, where T1 and T2 are time constants, s is the Laplace variable;
a first summation module (62) producing 12th signal representative (63) in response to said output signal (61) of said first low-pass filter (60) and said total air flow demand signal (51), computed as a difference between said total air flow demand signal (51) and said output signal (61);
a bias module for biasing of said 12th signal representative (63) and producing 13th signal representative (66) by summation of said 12th signal representative (63) and a constant bias signal (64);
a signal limiter (67) producing trim air flow demand signal (68) through a two-level saturation nonlinear function, in response to said 13th signal representative (66);
a second summation module (69) producing main air flow demand signal (70) in response to said total air flow demand signal (51) and said trim air flow demand signal (68), computed as a difference between said total air flow demand signal (51) and said trim air flow demand signal (68);
a main air actuated valve (29) for manipulating a larger part of a flow rate of said second feed stream of air;
a trim air actuated valve (33) for manipulating a smaller part of a flow rate of said second feed stream of air;

a main air flow sensor (17), being a part of said second flow sensor system, for establishing a 14th signal representative (18) of an actual flow rate of said air flowing through said main air actuated valve (29);

a trim air flow sensor (20), being a part of said second flow sensor system, for establishing a 15th signal representative (21) oft an actual flow rate of said air flowing through said trim air actuated valve (33);

a second proportional-integral-derivative controller (73), which compares said main air flow demand signal (70) and 14th signal representative (18) produces a $16^{th}$ signal representative (27) and supplies it as a command to said main air actuated valve (29);

a third proportional-integral-derivative controller (76), which compares said trim air flow demand signal (68) and $15^{th}$ signal representative (21), produces a $17^{th}$ signal representative (31) and supplies it as a command to said trim air actuated valve (33).

4. Apparatus as recited in claim 1 wherein said second computation module for establishing said principal air flow demand signal (49) further comprises a controller for computation of an air-to-acid gas ratio demand signal (47) and a multiplication module for multiplication of said air-to-acid gas ratio demand signal by said first signal representative (15).

5. Apparatus as recited in claim 4 wherein said controller for computation of said air-to-acid gas ratio demand signal (47) is an adaptive controller that comprises a division module (81) for producing a signal representative for actual air-to-acid gas ratio (82) at the input to said furnace through division of said second signal representative (53) by said first signal representative (15);

a fifth computation module for processing said signal representative for actual air-to-acid gas ratio (82), further comprising a sixth computation module (83) for computing an absolute value of an input signal and having an input signal being said sixth signal representative (43), and producing an output signal (84); a first comparator (85) having an input signal being said output signal (84) of said sixth computation module (83) and producing a Boolean output signal (86); a second low-pass filter (89) producing eighth signal representative (90) in accordance with the transfer function of a low-pass filter, which in a preferred embodiment is $W_{LPF2}(s)=1/[(T_3s+1)(T_4s+1)]$, where $T_3$ and $T_4$ are time constants, s is the Laplace variable; and a first selector (87) having two inputs being the output signal of said second low-pass filter (89) and said signal representative for actual air-to-acid gas ratio (82), and a control input being said Boolean output signal (86) of said comparator (85);

a third summation module (91) producing ninth signal representative (92) in response to an output signal (90) of said second low-pass filter (89) and said air-to-acid gas ratio demand (47), and computed as a difference between said output signal (90) of said second low-pass filter (89) and said air-to-acid gas ratio demand signal (47);

a nonlinear functional block (93) producing tenth signal representative (94) in response to said ninth signal representative (92) in accordance with the nonlinear characteristic of a dead band nonlinear function;

a fourth summation module (95) producing 11 th signal representative (96) in response to said output signal (94) of said nonlinear functional block (93) and said air-to-acid gas ratio demand signal (47);

a memory block (105) to store a value of computed air-to-acid gas ratio demand signal (104) and produce an output signal (106) being a memorized value of said computed air-to-acid gas ratio demand signal (104);

a seventh computation module for processing of said 11 th signal representative (96) through passing it to an input of said memory block (105) in response to said ninth signal representative, further comprising a second comparator (97) having an input being said ninth signal representative (92) and producing a Boolean output signal (98); a pulse generator (99) generating update request Boolean pulse signal (100) with adjustable frequency that in a preferred embodiment can be adjusted in the range from one pulse per 5 seconds to one pulse per 60 seconds; an AND logical block (101) having the first input being said output signal of said second comparator (97) and second input being said output signal of said pulse generator (99), and producing an output signal (102) in accordance with the AND Boolean operation; and a second selector (103) having the first input being said 11 th signal representative (96) and the second input being the output signal of said memory block (105), and a control input being said output signal (102) of said AND logical block (101);

an eighth computation module for producing said air-to-acid gas ratio demand signal (47) further comprising a module (107) for manual entry of a manual air-to-acid gas ratio demand value, which provides a manual air-to-acid gas ratio demand signal (108) necessary for a start-up operation of a system; an operator switch (110); and a third selector (109) having two inputs being said manual air-to-acid gas ratio demand signal (108) and said output signal (106) of said memory block (105), and a control input being the output signal of said operator switch (110); with the output of said selector (109) being said air-to-acid gas ratio demand signal (47).

6. Apparatus as recited in claim 1 wherein said third computation module for establishing said supplemental air flow demand signal (45) is a proportional-integral-derivative controller (44) having an input being said sixth signal representative (43).

7. Apparatus as recited in claim 1 wherein said third computation module for establishing said supplemental air flow demand signal (45) is a relay controller having an input being said sixth signal representative (43).

* * * * *